United States Patent [19]

DeChiara et al.

[11] Patent Number: 4,921,699
[45] Date of Patent: May 1, 1990

[54] POLYPEPTIDES HAVING INTERFERON ACTIVITY

[75] Inventors: Thomas M. DeChiara, Bloomfield; Stanley J. Tarnowski, Jr., Nutley, both of N.J.

[73] Assignee: Hoffman-La Roche Inc., Nutley, N.J.

[21] Appl. No.: 257,900

[22] Filed: Oct. 14, 1988

Related U.S. Application Data

[60] Division of Ser. No. 827,674, Feb. 10, 1986, Pat. No. 4,816,566, which is a continuation of Ser. No. 499,964, Jun. 1, 1983, abandoned.

[51] Int. Cl.$^5$ .................. A61K 45/02; C12N 15/00; C07H 21/04
[52] U.S. Cl. ........................... 424/85.7; 536/27; 435/320; 435/252.3; 435/69.51; 530/351
[58] Field of Search .............. 424/85.7; 530/351; 435/68, 320, 252.3, 252.33; 536/27

[56] References Cited

U.S. PATENT DOCUMENTS

| | | | |
|---|---|---|---|
| 4,457,867 | 7/1984 | Ishida | 260/112.5 R |
| 4,518,584 | 5/1985 | Mark et al. | 424/85 |
| 4,737,462 | 4/1988 | Mark et al. | 435/253 |

OTHER PUBLICATIONS

Arnheifer et al., Nature, 294: 278 (1981).
Shepard et al., Nature, 294: 563 (1981).

*Primary Examiner*—Blondel Hazel
*Attorney, Agent, or Firm*—George M. Gould; William H. Epstein

[57] ABSTRACT

A polypeptide having interferon activity which has an amino acid sequence corresponding to an amino acid sequence of an interferon selected from rIFN-α, hybrid rIFN-α, rIFN-β and rIFN-γ interferons in which at least one cysteine residue in the amino acid sequence has been replaced by an amino acid residue which is incapable of forming intermolecular disulfide bonds is provided. There are also provided a dsDNA sequence encoding the novel polypeptide; a replicable plasmidic expression vehicle containing the dsDNA encoding the novel polypeptides of the invention; a microorganism which has been transformed with the replicable plasmidic expression vehicle; and a method of preparing the dsDNA which encodes the novel polypeptides of the invention.

17 Claims, 6 Drawing Sheets

```
EcoRI        Sau3AI
AATTC ATG TGT GAT CTG CCT CAA ACC CAC AGC CTG GGT AGC AGG AGG ACC TTG
      MET Cys Asp Leu Pro Gln Thr His Ser Leu Gly Ser Arg Arg Thr Leu
       1                                  10

ATG CTC CTG GCA CAG ATG AGG AAA ATC TCT CTT TTC TCC TGC TTG AAG GAC AGA
MET Leu Leu Ala Gln MET Arg Lys Ile Ser Leu Phe Ser Cys Leu Lys Asp Arg
                 20                                  30

374
CAT GAC TTT GGA TTT CCC CAG GAG GAG TTT GGC AAC CAG TTC CAA AAG GCT GAA
His Asp Phe Gly Phe Pro Gln Glu Glu Phe Gly Asn Gln Phe Gln Lys Ala Glu
                     40                                  50

ACC ATC CCT GTC CTC CAT GAG ATG ATC CAG CAG ATC TTC AAT CTC TTC AGC ACA
Thr Ile Pro Val Leu His Glu MET Ile Gln Gln Ile Phe Asn Leu Phe Ser Thr
                         60

AAG GAC TCA TCT GCT GCT TGG GAT GAG ACC CTC CTA GAC AAA TTC TAC ACT GAA
Lys Asp Ser Ser Ala Ala Trp Asp Glu Thr Leu Leu Asp Lys Phe Tyr Thr Glu
 70                                  80

PvuII
CTC TAC CAG CAG CTG AAT GAC CTG GAA GCC TGT GTG ATA CAG GGG GTG GGG GTG
Leu Tyr Gln Gln Leu Asn Asp Leu Glu Ala Cys Val Ile Gln Gly Val Gly Val
             90                                 100

HinfI
ACA GAG ACT CCC CTG ATG AAG GAG GAC TCC ATT CTG GCT GTG AGG AAA TAC TTC
Thr Glu Thr Pro Leu MET Lys Glu Asp Ser Ile Leu Ala Val Arg Lys Tyr Phe
            110                                 120

CAA AGA ATC ACT CTC TAT CTG AAA GAG AAG AAA TAC AGC CCT TGT GCC TGG GAG
Gln Arg Ile Thr Leu Tyr Leu Lys Glu Lys Lys Tyr Ser Pro Cys Ala Trp Glu
                    130                                 140

GTT GTC AGA GCA GAA ATC ATG AGA TCT TTT TCT TTG TCA ACA AAC TTG CAA GAA
Val Val Arg Ala Glu Ile MET Arg Ser Phe Ser Leu Ser Thr Asn Leu Gln Glu
                        150

AGT TTA AGA AGT AAG GAA TGA
Ser Leu Arg Ser Lys Glu
```

FIG. I

POLYPEPTIDES HAVING INTERFERON ACTIVITY

This is a division of application Ser. No. 06/827,674, filed Feb. 10, 1986 now U.S. Pat. No. 4,816,566, which is a continuation of Ser. No. 499,964, filed June 1, 1983, now abandoned.

BACKGROUND OF THE INVENTION

Interferons are proteins which are produced by a number of different kinds of organisms and which are presently grouped into three major classes, designated leukocyte interferon (IFN-$\alpha$), fibroblast interferon (IFN-$\beta$) and immune interferon (IFN-$\gamma$). The interferons have antiviral and antiproliferative activities, a potent ability to confer a virus-resistant state in targeted cells and immunomodulatory activities. Their biological properties have led to the clinical use of interferons as therapeutic agents for the treatment of viral infections and malignancies.

Interferons have been produced from natural sources such as buffy coat leukocytes and fibroblast cells, optionally using known inducing agents to increase the production of interferon. Interferons have also been produced by recombinant DNA techniques, i.e. by expression from a microorganism which has been transformed with an expression vector containing an interferon gene under the control of a promoter-operator sequence. (Leukocyte, fibroblast and immune interferons produced by recombinant techniques are designated rIFN-$\alpha$, rIFN-$\beta$ and rIFN-$\gamma$, respectively). As many as 12 distinct genes encoding for different species of rIFN-$\alpha$ have been cloned. These various species are designated rIRN-$\alpha$A, rIFN-$\alpha$B, rIFN-$\alpha$C and so forth.

Goeddel and coworkers achieved the initial expression of rIFN-$\alpha$A in *E. coli* cells containing the recombinant plasmid pL 31. (Nature, 287, 411 (1980)). This plasmid contains the structural gene for mature rIFN-$\alpha$A (i.e., a gene in which the nucleotide sequence encoding a 23-amino acid signal peptide normally translated in the human cell has been removed and an ATG "start" signal has been inserted immediately before the codon for the first amino acid following the signal peptide) under the control of an appropriately positioned promoter-operator sequence. The rIFN-$\alpha$A produced in this manner has been employed in the clinical treatment of patients suffering from a variety of viral and neoplastic diseases.

The rIFN-$\alpha$ interferons are 165 amino acids (in the case of rIFN-$\alpha$A) or 166 amino acids in length, except that they may, in some instances contain a methionine attached to the N-terminus of the ordinarily first amino acid of the protein as the result of translation of the ATG start signal which encodes methionine.

Hybrid leukocyte interferons have been produced by expression of genes which are produced by cleaving two or more genes encoding different leukocyte interferons at internal endonuclease cleavage sites and then ligating one or more cleavage fragments of one gene with one or more cleavage fragments of a different gene (or genes) to produce a gene encoding a complete 165- or 166-amino acid leukocyte interferon having one or more segments corresponding to a portion of a first leukocyte interferon species and one or more segments corresponding to portions of different leukocyte interferon species. In this manner, for example, it has been possible to produce a leukocyte interferon in which the amino acid sequence corresponds to that of rIFN-$\alpha$A at positions 1-92 and to that of rIFN-$\alpha$D at positions 92-166. Similarly, by ligating the gene cleavage fragments in reverse order, it has been possible to produce a leukocyte interferon in which the amino acid sequence corresponds to that of rIFN-$\alpha$D at positions 1-92 and to that of rIFN-$\alpha$A at positions 93-165. (J. Biol. Chem., 257, pp. 11497-11502 (1982)).

A problem which has occurred in the manufacture and use of interferons is that the individual interferon molecules tend to oligomerize. The etiology of these oligomers has not been completely understood. It is believed, however, that the procedures used to purify interferons for therapeutic use may contribute to the oligomerization problem. Presently available purification methods, such as high pressure liquid chromatography or monoclonal antibody affinity chromatography are carried out under conditions which can favor the formation of dimers, trimers and higher oligomers of interferon. These oligomeric forms of interferon result from two or more interferon molecules becoming irreversibly associated with one another through intermolecular covalent bonding, such as by disulfide linkages. This problem has been observed particularly with respect to leukocyte and fibroblast interferons.

While the dimeric forms of interferons are believed to retain biological activity, the higher oligomeric forms in many cases have either no biological activity or significantly reduced activity by comparison to the monomeric forms. Moreover, the oligomeric forms have the potential for causing deleterious side effects if used therapeutically.

All of the known rIFN-$\alpha$, rIFN-$\beta$ and rIFN-$\gamma$ interferons contain multiple cysteine residues. These residues contain sulfhydryl side-chains which are capable of forming intermolecular disulfide bonds, which result in oligomerization, as well as intramolecular disulfide bonds. The amino acid sequence of rIFN-$\alpha$A contains cysteine residues at positions 1, 29, 98 and 138. Wetzel and coworkers assigned intramolecular disulfide bonds between the cysteine residues and positions 1 and 98 and between the cysteine residues and positions 29 and 138. Nature, 289, 606 (1981).

Because of the importance of eliminating or preventing the occurrence of oligomers in interferon preparations, considerable efforts have been expended to overcome the oligomerization problem. Heretofore, efforts have been concentrated on adjusting the purification conditions to prevent the formation of oligomers or post-processing with reagents and reaction conditions which reduce intermolecular disulfide bonds.

BRIEF DESCRIPTION OF THE INVENTION

This invention relates to novel proteins which display the biological activities of the known interferons without the concomitant problem of oligomerization that is associated with the known interferons. In particular, we have prepared novel polypeptides which correspond in amino acid sequence to known interferons, except that certain cysteine residues have been replaced by residues of other amino acids which are incapable of forming disulfide bonds. Quite surprisingly, we have been able to make these amino acid substitutions without any diminution in the biological activity of the resultant protein as compared to that of the known interferon from which it was derived.

In one broad aspect, this invention relates to a novel polypeptide having interferon activity comprising an amino acid sequence corresponding to an amino acid sequence of an interferon selected from rIFN-α, hybrid rIFN-α, rIFN-β and rIFN-γ interferons in which at least one cysteine residue has been replaced by an aminoacid residue which is incapable of forming intermolecular disulfide bonds, i.e. an amino acid residue other than cysteine.

In a preferred embodiment of this broad aspect, the invention relates to a polypeptide comprising an amino acid sequence corresponding to an amino acid sequence of rIFN-αA in which at least one of the cysteine residues at positions 1 and 98 has been replaced by an amino acid residue which is incapable of forming intermolecular disulfide bonds.

This broad aspect of the invention also relates to antiviral compositions comprising the novel polypeptides, wherein the composition is essentially free of oligomers of higher aggregation than the dimeric form and in one preferred embodiment, contains only stable monomeric interferon.

In a second broad aspect, this invention relates to methods and intermediates for producing the novel polypeptides described above by the techniques of DNA recombination. In particular, this aspect relates to a method of producing a double stranded DNA (dsDNA) encoding the novel polypeptide by using restriction enzymes to excise a portion of the dsDNA encoding for the undesired cysteine residue in the parental interferon gene and replacing it with a synthetic oligodeoxynucleotide segment in which the nucleotide triplet encoding the cysteine residue has been replaced by a nucleotide triplet encoding an amino acid residue which is incapable of forming intermolecular disulfide bonds.

Accordingly, this second broad aspect of the invention encompasses dsDNA which encodes the novel polypeptides of the invention; a replicable plasmidic expression vehicle containing the dsDNA encoding the novel polypeptides of the invention; a mircoorganism which has been transformed with the replicable plasmidic expression vehicle; and a method of preparing the dsDNA which encodes the novel polypeptides of the invention.

BRIEF DESCRIPTION OF THE DRAWINGS

FIG. 1 is a representation of the amino acid sequence of rIFN-αA and a nucleotide sequence which encodes rIFN-αA.

Figure 2:
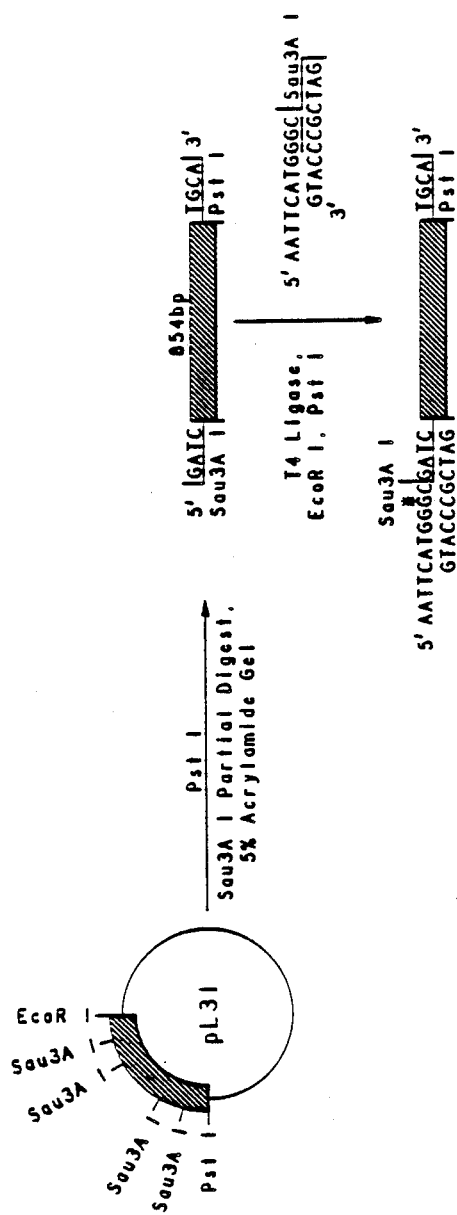
FIG. 2 is a schematic representation of the process used to produce the dsDNA encoding rIFN-αA (Gly 1).

Asterisks in the figures indicate nucleotide substitutions replacing the nucleotide triplets encoding cysteines.

DETAILED DESCRIPTION OF THE INVENTION

I. The Novel Polypeptides and Compositions

As previously indicated, the invention relates to a novel polypeptide having interferon activity comprising an amino acid sequence corresponding to an amino acid sequence of an interferon selected from rIFN-α, hybrid rIFN-α, rIFN-β and rIFN-γ interferons in which at least one cysteine residue in the amino acid sequence has been replaced by an amino acid residue which is incapable of forming intermolecular disulfide bonds, i.e. a residue other than cysteine.

The amino acid structures of the parental interferons which can be modified by replacement of cysteine residues to produce the novel polypeptides are known in the art. The cloning and expression of rIFN-αA was described by Goeddel and coworkers in Nature, 287, 411 (1980). FIG. 1 gives the amino acid sequence of mature rIFN-αA. The line above the amino acid sequence gives the associated nucleotide sequence of a coding strand of dsDNA which encodes the mature rIFN-αA. Other species of rIFN-α's can also be modified to produce the novel polypeptides of the invention. The amino acid sequences of rIFN-αA, B, C, D, F, G, H, K and L, as well as the nucleotide sequences which encode them are described by Pestka in Archiv. Biochem. Biophys., 221, 1 (1983). The amino acid sequences and associated nucleotide sequences of rIFN-αE, I and J are described in British Patent Specification No. 2,079,291, published Jan. 20, 1982.

The novel polypeptides of the invention can also be produced by modifying the amino acid structure of a hybrid rIFN-α. As used herein, the term "hybrid rIFN-α" refers to a leukocyte interferon derived from a transformant microorganism by the expression of a gene which encodes a leukocyte interferon in which one or more segments of the molecule correspond to a segment of a first leukocyte interferon species and one or more other segments correspond to segments of different leukocyte interferon species. Exemplary of such hybrids are hybrids of rIFN-αA and rIFN-αD which are disclosed by Pestka in Archiv. Biochem. Biophys., 221, 1 (1983).

The cloning and expression of mature rIFN-β is described by Goeddel et al. in Nucleic Acids Research, 8, 4057 (1980). The amino acid structure, as well as the nucleotide sequence which encoded the amino acid structure, are given in the publication.

The cloning and expression of mature rIFN-γ are described by Gray, P. W. et al., in Nature, 295, 503 (1982). The amino acid structure and the nucleotide sequence which encoded the amino acid sequence are given.

The novel polypeptides of this invention can also be prepared by the modification of parental interferons which represent allelic variations of the specific rIFN-α, hybrid rIFN-α, rIFN-β and rIFN-γ interferons of the publications cited in the preceding paragraphs. For example, Nagata and coworkers described the expression of an rIFN-α gene (denoted as rIFN-α$_1$) which expressed a polypeptide (in non-mature form) which differs from rIFN-αD by a single amino acid at position 114. (Nature, 284, 316 (1980)). Similarly the cloning and expression of an rIFN-α gene (identified as rIFN-α2) which expressed a polypeptide differing from rIFN-αA by a single amino acid at position 23 was described in European Patent Application No. 32 134, published July 15, 1981. DNA sequences encoding these and other allelic variations of the parental rIFN's can be modified to encode the novel polypeptides of this invention, provided that the parental rIFN contains a cysteine residue which is not required for biological activity and which is capable of participating in the formation of intermolecular disulfide bonds.

Preferred polypeptides of the invention are those obtained by substitution of cysteine residues in rIFN-α's or hybrid-α's. All the rIFN-α's, and consequently all hybrid rIFN-α's, contain cysteine residues at the N-terminus, i.e. at position 1, and at position 29, except for rIFN-αE, which does not have cysteine at position 29. Additionally, rIFN-αA contains cysteine residues at positions 98 and 138; rIFN-αB contains cysteine residues at positions 100 and 139; rIFN-αC, F, G, H, I, J, K and L contain cysteine residues at positions 99 and 139; and rIFN-αD contains cysteine residues at positions 86, 99 and 139. We note that Pestka, in Archiv. Biochem. Biophys., 221, 1 (1983), shows cysteine residues at positions 99 and 139 of rIFN-αA in FIG. 17 of the article, rather than at positions 98 and 138. This is because the sequence representation has been shifted one position following position 43 to align it with the other rIFN-α species which contain one more amino acid residue than rIFN-αA. All amino acid positions recited herein refer to sequentially numbered amino acids and do not account for such shifts.

The polypeptides of the invention have amino acid sequences corresponding to amino acid sequences of known rIFN's in which cysteine residues have been replaced by amino acid residues which are incapable of forming intermolecular disulfide bonds. The cysteine residues which are replaced are those which are not required for the rIFN to maintain interferon activity. As used herein the term "interferon activity" refers to the characteristic antiviral and antigrowth activity characteristic of the interferons. The characteristic antiviral activity of rIFN can be determined using the cytophatic effect inhibition test described in Familleti, P. C. et al., Methods in Enzymology 78, 387 (1981). The characteristic antigrowth activity of rIFN can be determined using the procedure described in Evinger, M. & Pestka, S., Methods in Enzymology, 79, 45 (1981).

Since the intramolecular disulfide bridge between the cysteine residues at positions 29 and 138 of rIFN-αA is believed to be required for interferon activity, we have left these residues intact. Similarly, the cysteine residues at positions 29 and 139 of rIFN-αB through L (or allelic variations thereof) are not replaced.

It has also been shown by Shepard et al. (Nature, 294, 563 565 (1981)) that substitution of the cysteine at position 141 of rIFN-β resulted in a loss of biological activity. Accordingly, this cysteine resiude is not to be replaced.

We have replaced the cysteine residue at position 1 of rIFN-αA, and we have replaced both cysteine residues at positions 1 and 98 of rIFN-αA, without any concomitant loss of interferon activity. Analogously, the cysteine residues at position 1 and/or position 99 (in the case of rIFN-αC through L) and 100 (in the case of rIFN-αB) can be replaced. In the case of a hybrid rIFN-α, cysteine residues may be replaced at position 1 and/or position 98, 99 or 100, depending upon which parental rIFN corresponds to that segment of the hybrid rIFN-α.

In the case of rIFN-αD or a hybrid rIFN-α in which a portion of the amino acid sequence corresponds to a portion of the amino acid sequence of rIFN-αD which contains position 87, the cysteine residue at position 87 may also be replaced.

The amino acid residues which replace the cysteine residues of the parental interferons in the polypeptides of the invention can be any amino acid residues which are incapable of participating in the formation of intermolecular disulfide bonds; that is, any amino acid residues other than cysteine. In the case of the N-terminal cysteine residue, i.e. the residue at position 1, we prefer to replace this with glycine, since glycine does not have a reactive side chain. In the case of the internal cysteine residues, eg. the residue at position 98 of rIFN-αA, we prefer to replace these with serine, since the serine side chain most closely resembles the spatial arrangement of the cysteine side chain. Thus, substitution with serine presents the least possibility for disrupting the conformation of the molecule.

We note that the rIFN-α, hybrid rIFN-α, and rIFN-γ interferons possess a cysteine residue at position 1. If desired, one can produce a novel polypeptide having interferon activity by deleting this cysteine entirely. This can be done by excising a portion of the gene for the parental interferon which encodes the N-terminal cysteine, in a manner such as that described in Example 1 herein and replacing it with a synthetic oligodeoxynucleotide corresponding to the excised portion of the gene except that the nucleotide triplet encoding the cysteine has been deleted; that is, the ATG translation initiation signal is immediately followed by the nucleotide triplet encoding the amino acid residue at position 2 of the parental interferon. The resultant dsDNA can be incorporated into an expression vehicle which can be used to transform a microorganism. The transformant microorganism can then be grown up and used to express a novel polypeptide having interferon activity which comprises an amino acid sequence corresponding to the amino acid sequence of an rIFN-α, hybrid rIFN-α, or rIFN-γ interferon in which the cysteine residue at position 1 has been deleted.

In a preferred embodiment of the invention, we have modified a gene encoding rIFN-αA (the amino acid sequence of which is given in FIG. 1), in a manner described in detail hereinafter, and expressed the gene to produce a polypeptide in which one or both cysteines at positons 1 and 98 have been replaced by amino acid residues which are incapable of forming intermolecular disulfide bonds. Accordingly, a preferred embodiment of our invention is a polypeptide of the formula R$^1$ ASP LEU PRO GLN THR HIS SER LEU GLY SER
ARG ARG THR LEU MET LEU LEU ALA GLN MET
ARG LYS ILE SER LEU PHE SER CYS LEU LYS ASP
ARG HIS ASP PHE GLY PHE PRO GLN GLU GLU PHE
GLY ASN GLN PHE GLN LYS ALA GLU THR ILE PRO
VAL LEU HIS GLU MET ILE GLN GLN ILE PHE ASN
LEU PHE SER THR LYS ASP SER SER ALA ALA TRP
ASP GLU THR LEU LEU ASP LYS PHE TYR THR GLU
LEU TYR GLN GLN LEU ASN ASP LEU GLU ALA
R$^2$ VAL ILE GLN GLY VAL GLY VAL THR GLU THR
PRO LEU MET LYS GLU ASP SER ILE LEU ALA VAL
ARG LYS TYR PHE GLN ARG ILE THR LEU TYR LEU
LYS GLU LYS LYS TYR SER PRO CYS ALA TRP GLU
VAL VAL ARG ALA GLU ILE MET ARG SER PHE
SER LEU SER THR ASN LEU GLN GLU -continued

SER LEU ARG SER LYS GLU wherein at least one of $R^1$ and $R^2$ is an amino acid residue having a side chain which is incapable of participating in the formation of an intermolecular disulfide bond and the other is cysteine or an amino acid having a side chain which is incapable of participating in the formation of an intermolecular disulfide bond.

Initially, we modified the gene for rIFN-αA by excising a portion of the gene which included the nucleotide triplet encoding cysteine at position 1 and replacing it with a synthetic oligodeoxynucleotide that encoded glycine at position 1. The section of the gene containing the nucleotide triplet for the cysteine at position 98 was unchanged. The modified gene in a plasmidic expression vehicle, was expressed in transformed E. coli to produce a polypeptide whose amino acid sequence corresponded to the amino acid sequence of rIFN-αA except that it contained a glycine at position 1 (the modified polypeptide is referred to herein as rIFN-αA (Gly 1)). After extraction from the cells and purification on a monoclonal antibody immunoaffinity chromatography column, the interferon thus obtained was subjected to electrophoresis on sodium dodecylsulfate polyacrylamide gel. Upon electrophoresis the interferon separated into a major band, corresponding to nomomeric material, and a minor band, corresponding to dimeric material. An rIFN-αA expressed from the unmodified gene for rIFN-αA was electrophoresced on the same gel and separated into bands corresponding to monomer, dimer and oligomers of higher aggregation than dimer, e.g trimer, tetramer, etc The composition containing a major proportion (more than half) of monomeric rIFN-αA (Gly 1) and a minor proportion of dimeric rIFN-αA (Gly 1) displayed the full antiviral activity characteristic of rIFN-αA on MDBK cells.

The gene containing the synthetic oligodeoxynucleotide segment encoding glycine at position 1 was further modified by excising a segment of the gene encoding cysteine at position 98 and replacing it with a synthetic oligodeoxynucleotide that encoded serine at position 98. This gene, in a plasmidic expression vehicle, was expressed in transformed E. coli to produce a polypeptide whose amino acid sequence corresponded to the amino acid sequence of rIFN-αA except that it contained glycine at position 1 and serine at position 98. (The modified polypeptide is referred to herein as rIFN-αA (Gly 1/Ser 98)). After extraction from cells and purification by monoclonal antibody immunoaffinity chromatography column, the interferon thus obtained was subjected to electrophoresis on sodium dodecylsulfate polyacrylamide gel. The interferon migrated in a single band, indicating essentially only monomeric material.

The composition comprising essentially all monomeric rIFN-αA (Gly 1/Ser 98) displayed antiviral activity which was about the same as that of rIFN-αA on MDBK cells.

The novel polypeptides of the invention can be used for the same purposes as the known interferons, eg. as antiviral and antitumor agents and as a treatment for immunosupressive conditions. Dosage and dose rate may parallel that currently being used in clinical applications of the known interferons, typically about $1-200 \times 10^6$ units daily. The polypeptides can be conveniently administered in parenteral dosage form. Suitable dosage forms can be prepared using known formulation methods to prepare pharmaceutically useful compositions wherein the polypeptide is admixed with a pharmaceutically acceptable carrier vehicle. A suitable dosage form will comprise an effective amount of the polypeptide together with a pharmaceutically acceptable carrier vehicle suitable for the particular host and mode of administration II. Recombinant DNA Methods and Intermediates As previously indicated, the novel polypeptides of this invention can be prepared, using the techniques of DNA recombination, by modifying a gene which encodes an rIFN-α, hybrid rIFN-α, rIFN-β or rIFN-γ to produce a gene which encodes the novel polypeptide; incorporating the modified gene into a replicable plasmidic expression vehicle; transforming a host microorganism with the expression vehicle containing the modified gene; growing up the transformed microorganism; expressing the polypeptide in the microorganism; and recovering the expressed polypeptides. One or more portions of the gene encoding the parental interferon, e.g. rIFN-αA, which contain the nucleotide triplets encoding the cysteine residues which are to be replaced, are excised and replaced with synthetic oligodeoxynucleotides encoding the desired sequence(s) having amino acid residues which are incapable of forming intermolecular disulfide bonds.

In a preferred embodiment of the invention, a gene encoding rIFN-αA (which is illustrated in FIG. 1) is modified to produce a double stranded DNA comprising a coding strand and a complementary strand, wherein the coding strand, reading from the 5' end comprises the sequence X GAT CTG CCT CAA ACC CAC AGC CTG GGT AGC
AGG AGG ACC TTG ATG CTC CTG GCA CAG ATG
AGG AAA ATC TCT CTT TTC TCC TGC TTG AAG
CAC AGA CAT GAC TTT GGA TTT CCC CAG GAG
GAG TTT GGC AAC CAG TTC CAA AAG GCT GAA
ACC ATC CCT GTC CTC CAT GAG ATG ATC CAG
CAG ATC TTC AAT CTC TTC AGC ACA AAG GAC
TCA TCT GCT GCT TGG GAT GAG ACC CTC CTA
GAC AAA TTC TAC ACT GAA CTC TAC CAG CAG
CTG AAT GAC CTG GAA GCC Y GTG ATA CAG
GGG GTG GGG GTG ACA GAG ACT CCC CTG ATG
AAG GAG GAC TCC ATT CTG GCT GTG AGG AAA
TAC TTC CAA AGA ATC ACT CTC TAT CTG AAA
GAG AAG AAA TAC AGC CCT TGT GCC TGC GAG
GTT GTC AGA GCA GAA ATC ATG AGA TCT
TTT TCT TTG TCA ACA AAC TTG CAA GAA
AGT TTA AGA AGT AAG GAA wherein at least one of X and Y is a nucleotide triplet encoding an amino acid residue which has a side chain that is incapable of forming an intermolecular disulfide bond and the other is a nucleotide triplet encoding cysteine or an amino acid residue which is incapable of forming an intermolecular disulfide bond.

In particular, we have provided a method of producing a double stranded DNA encoding a polypeptide having interferon activity which comprises:

(a) cleaving a double stranded DNA which contains a sequence encoding an interferon selected from rIFN-α, hybrid rIFN-α, rIFN-β and rIFN-γ interferons by endonuclease cleavage to prouce a first cleavage fragment containing a nucleotide triplet encoding a cysteine residue and one or more other cleavage fragments encoding the remainder of the interferon;

(b) separating the cleavage fragment containing the nucleotide triplet encoding the cysteine from the cleavage fragments encoding the remainder of the interferon;

(c) preparing a double stranded oligodeoxynucleotide sequence corresponding to the separated cleavage fragment in which the nucleotide triplet encoding said cysteine residue has been replaced by a nucleotide triplet encoding an amino acid residue which is incapable of forming intermolecular disulfide bonds, said double stranded oligodeoxy-nucleotide having ends complementary to the ends of the double stranded DNA encoding the remainder of the interferon; and (d) ligating said double stranded oligodeoxynucleotide to the double stranded DNA encoding the remainder of the interferon in the proper orientation for the expression of the polypeptide.

As used herein the term "upstream" refers to the direction moving toward the 5' end of the coding strand and the term "downstream" refers to the direction moving toward the 3' end of the coding strand.

The dsDNA encoding an rIFN which is cleaved in step (a) above can be conveniently obtained from an expression vector or cloning vector containing the structural gene. As a source of dsDNA to serve as a starting material from which to prepare the dsDNA encoding rIFN-αA (Gly 1) and rIFN-αA (Gly 1/Ser 98), we employed plasmid pL 31 This plasmid, derived from pBR322, contains a 1160 base pair insert encoding a trp promoter-operator, ribosome binding site, ATG translation initiation signal, a structural gene encoding the amino acid sequence of rIFN-αA depicted in FIG. 1 and an untranslated 3' sequence following the stop codon (Goeddel et al., Nature, 287 411 (1980)).

The endonucleases which are used to cleave the dsDNA in step (a) are well known to those familiar with the techniques of DNA recombination. They are restriction enzymes which selectively recognize and cleave certain specific DNA sequences. The particular endonucleases used will depend on the particular rIFN gene involved and the particular cysteine residue(s) to be replaced. It is well within the skill level of the worker in the art to identify appropriate cleavage sites and to select an appropriate cleavage endonuclease. The reaction conditions under which the cleavage reactions take place, as well as the methods for separating and purifying the fragments, are well known in the art.

In preparing a dsDNA sequence encoding rIFN-αA (Gly 1), we took advantage of the existence of a Sau 3AI recognition site which cleaves the structural gene for rIFN-αA immediately following the nucleotide triplet of the coding strand which codes for cysteine at position 1 to separate the nucleotide triplet encoding the undesired cysteine from the remainder of the structural gene.

The procedure which we employed to produce a dsDNA encoding rIFN-αA (Gly 1) can be described as follows, with specific reference to FIG. 2. The plasmid pL 31, which contained the structural gene for rIFN-αA (the coding strand of which is depicted in FIG. 1), was digested completely with Pst I and partially with Sau 3AI. An 854 base pair cleavage fragment was isolated. This fragment, beginning at the Sau 3AI site contained the full sequence of bases encoding rIFN-αA except for the TGT encoding cysteine at position 1 and terminated at the Pst I site 360 bases beyond the stop codon on the coding strand.

The 5' end of the rIFN-αA gene thus removed was replaced by ligating the 854 base pair segment with the synthetic oligodeoxynucleotide

in which the —GGC— encoding a glycine residue replaces the —TGT— encoding cysteine in the unmodified rIFN-αA gene. The 865 base pair dsDNA thus produced contained the sequence encoding rIFN-αA (Gly 1) and terminated at an Eco RI site at the 5' end of the coding strand and a Pst I site at the other end.

In order to modify the rIFN gene to replace an internal cysteine residue, e.g. the cysteine residue at position 98 of rIFN-αA or rIFN-αA (Gly 1), the dsDNA encoding the rIFN can be cleaved at a first endonuclease cleavage site upstream of the nucleotide triplet encoding the undesired cysteine and at a second endonuclease cleavage site downstream of the nucleotide triplet encoding the undesired cysteine to isolate a fragment containing the undesired nucleotide triplet. The fragment containing the undesired nucleotide triplet is separated from the dsDNA encoding the remainder of the rIFN. A synthetic oligodeoxynucleotide is prepared which corresponds to the removed segment except that the nucleotide triplet encoding cysteine is replaced by a nucleotide triplet encoding a different amino acid residue, preferably serine. This synthetic oligodeoxynucleotide is then ligated in the proper orientation to the dsDNA encoding the remainder of the rIFN.

If it is desired to delete two internal cysteine residues which are sufficiently close together, this may be done by cleaving the gene at a first endonuclease cleavage site upstream of the nucleotide triplet encoding the first undesired cysteine residue and at a second endonuclease cleavage site downstream of the nucleotide triplet encoding the second undesired cysteine; and replacing the segment thus removed with a synthetic oligodeoxynucleotide encoding a segment in which both cysteines are replaced by different amino acids.

Figure 3:
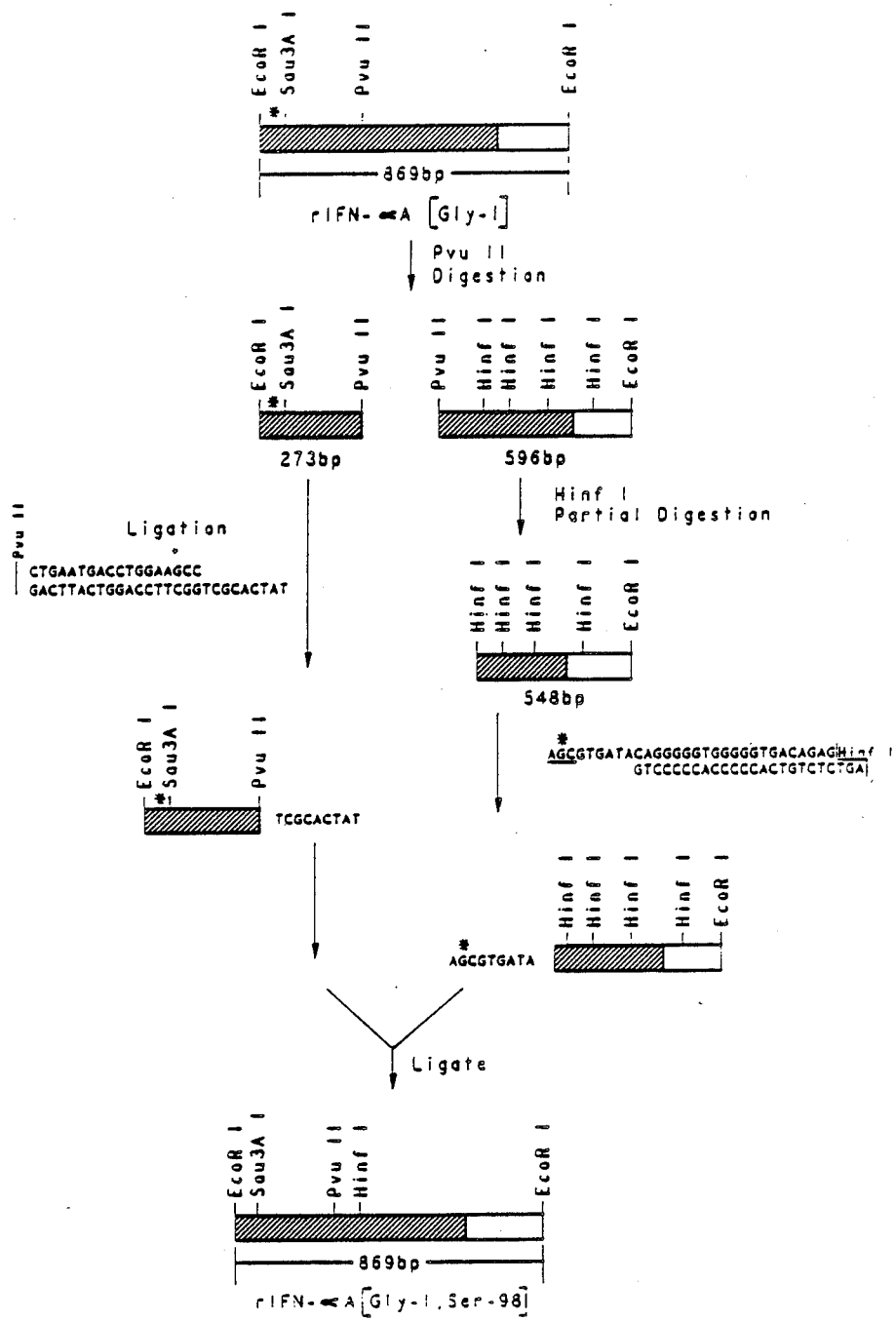
FIG. 3 is a schematic representation of the process used to produce the dsDNA encoding rIFN-αA (Gly 1/Ser 98).

With reference to FIG. 3, we used the following procedure to produce a dsDNA encoding rIFN-αA (Gly 1/Ser 98). The starting material employed was an 869 base pair dsDNA encoding rIFN-αA (Gly 1). This was the 865 base pair of dsDNA produced by the previously described procedure to which an additional 4 base pairs had been ligated to the 3' end in order to create a terminal Eco RI recognition site for insertion into an expression vector. This dsDNA was cleaved with Pvu II, resulting in a 273 base pair segment containing the 5' end of the coding strand for rIFN-αA (Gly 1) and a 596 base pair segment containing the 3' end of the coding strand for rIFN-αA (Gly 1), which included the nucleotide triplet encoding cysteine at position 98. The 596 base pair segment was partially digested with Hinf I to produce a 48 base pair fragment containing the nucleotide triplet encoding the cysteine at position 98 and a 548 base pair fragment encoding the remainder of the 3' end. Two synthetic double stranded oligodeoxynucleotide were prepared to replace the 48 base pair region. The synthetic double stranded oligodeoxynucleotides, which contained a 9-base overlapping region, had the following sequences:

```
5'  CTGAATGACCTGGAAGCC
3'  GACTTACTGGACCTTCGGTCGCACTAT
    Pvu II       Block I
```

```
5' AGCGTGATACAGGGGGTGGGGGTGACAGAG  Hinf I
3'         GTCCCCCACCCCCACTGTCTCTGA
                    Block II
```

The AGC nucleotide triplet encoding serine in Block II replaces the TGT encoding cysteine in the deleted 48 base pair fragment. Block I was ligated to the 273 base pair fragment and Block II was ligated to the 548 base pair fragment of the gene. The resulting two fragments were ligated at the 9-base overlap to produce an 869 base pair dsDNA containing a coding strand which encoded rIFN-αA (Gly 1/Ser 98).

The dsDNA encoding the novel polypeptide of the invention can be incorporated into an expression vehicle which can be used to transform a host microorganism for the purpose of expressing the novel polypeptide. Any of the known and commonly employed expression vectors may be employed for this purpose, particularly plasmidic expression vectors. A plasmid is a non-chromosomal loop of double stranded DNA found in bacteria and other microbes, often in multiple copies per cell. Included in the information encoded in the plasmid DNA is that required to reproduce the plasmid in daughter cells (i.e. a "replicon") and, ordinarily, one or more selection characteristics such as, in the case of bacteria, resistance to antibiotics which permit clones of the host cell containing the plasmid of interest to be recognized and preferentially grown in selective media.

A plasmidic expression vector must also incorporate the control elements necessary to regulate expression of the structural gene. Expression is initiated in a region known as the promoter which is recognized by and bound by RNA polymerase. In some cases, as in the lambda phage or "$P_L$" promoter which we employed in the practice of the present invention, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to its 3' end into messenger RNA which is in turn translated into a polypeptide having the amino acid sequence for which the DNA encodes. Each amino acid is encoded by a nucleotide triplet or "codon" within the structural gene, i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome bindng site are positioned properly with respect to the AUG initiator codon and if all remaining codons follow the initiator codon in phase.

To incorporate the dsDNA encoding the novel polypeptide of the invention into the expression vector, the vector is first linearized by cutting it with an endonuclease at a cleavage site which is appropriately positioned with respect to the promoter-operator sequence to allow expression of the inserted structural gene. The dsDNA encoding the novel polypeptide is then ligated at either end to the cleaved ends of the vector to recircularize the vector. Of course, the ends of the dsDNA insert must be complementary to the cleaved ends of the vector to allow ligation. If necessary, the dsDNA can be rendered complementary by building up or cleaving back the ends, using known procedures, to provide complementary ends, provided that the structural gene itself and the associated initiation and termination codons are left intact and that the gene remains in the proper position and reading frame with respect to the promoter-operator sequence to allow expression.

Accordingly, there is provided, in accordance with the teachings of this invention, a replicable plasmidic expression vehicle comprising:
  (a) a replicon;
  (b) a promoter-operator sequence;
  (c) a DNA sequence encoding a ribosome binding site; and
  (d) a DNA sequence, in phase with said promoter-operator sequence, comprising a translation initiation signal, a sequence encoding a polypeptide having interferon activity, said polypeptide comprising an amino acid sequence of an interferon selected from rIFN-α, hybrid rIFN-α, rIFN-β and rIFN-γ interferons in which at least one cysteine residue in the amino acid sequence has been replaced by an amino acid residue which is incapable of forming intermolecular disulfide bonds, and a translation termination signal.

Any of the known plasmidic expression vectors can be employed in the preparation of the replicable plasmidic expression vehicle of this invention. We prefer to employ plasmid pRC 23, an expression vector which is derived from pBR 322 and incorporates the $P_L$ promoter-operator sequence (Bernard, H. U. and Helinski, D. R., Methods in Enzymology, 68, 482). The vector pRC 23 is constructed by ligating synthetic oligodeoxynucleotides containing a "consensus" rebisome binding site (Scherer et al., *Nucleic Acids Research* 8, 3895 (1980)) to a 250 bp Bgl II-Hae III fragment containing the $P_L$ promoter and inserting the ligation product into the plasmid pRC 2. Further details concerning the construction of the cloning and expression vector pRC 23 can be obtained by reference to U.S. patent application Ser. No. 397,388, filed July 12, 1982 entitled "Novel Vectors and Methods for Controlling Interferon Expression", inventor Robert M. Crowl. In this vector, the operator is recognized by a temperature-sensitive repressor protein which is inactive at a temperature above about 36° C.; that is, it does not bind the operator at a temperature above 36° C. The repressor protein is encoded by the cIts gene, which is carried on a compatible plasmid pRK 248. Thus transcription and expression of gene can be controlled by controlling the temperature at which the recombinant microorganism incorporating the expression vehicle is maintained. Plasmic pRC 23 is designed to accept dsDNA sequences which terminate in Eco RI recognition sites. Accordingly, the 869 base pair dsDNA sequences previously mentioned, which encode either rIFN-αA (Gly 1) or rIFN-αA (Gly 1/Ser 98) and terminate in Eco RI recognition sites at either end, can be inserted directly into pRC 23 which has been linearized by cleavage with Eco RI. Ligation is carried out under known conditions using a known ligase e.g. T4 DNA ligase.

The replicable plasmidic expresion vehicle is used to transform a microorganism, preferably an *E. coli*, to produce a transformant which is capable of expressing the polypeptide of the invention. Transformation can be conveniently carried out using known procedures such as treating the host cells with CaCl₂ at about 4° C. to render the cell walls permeable to the replicable plasmidic expression vehicle (see, e.g. Humphries et al., *Transformation*, eds. Glover & Butler, 287 312 (1979)). The transformed microorganism can be grown up under known fermentation conditions and the novel polypeptide expressed in the microorganism. The polypeptide is then recovered, for example, by lysing the cells to release the polypeptide and purifying the polypeptide by known techniques. We prefer to purify the polypeptide by immunoaffinity chromatography on a column having monoclonal antibodies to the corresponding parental rIFN bound to a solid support. A suitable monoclonal antibody for use in purifying rIFN-αA (Gly 1) or rIFN-αA (Gly 1/Ser 98) is described by Staehelin et al. in Journal of Biological Chem., 256, 9750 (1981).

When the expression vector employed to produce the replicable plasmidic expression vehicle is pRC 23, the resultant transformant microorganism can be grown up to a desired density at a temperature of 30° C. and the tempperature can then be raised to about 42° C., to inactivate the repressor protein and initiate expression.

The following examples are presented in order to further illustrate the practice of this invention and are not intended to limit the invention in any way. Unless otherwise stated, all parts and percents are by weight and all temperatures are centigrade.

EXAMPLE 1

Preparation of rIFN-αA (Gly 1)

(a) Preparation of dsDNA Encoding rIFN-αA (Gly 1)

Plasmid pL 31 (6 μg) containing the gene encoding rIFN-αA, was digested completely with Pst I and partially Sau 3AI. Both digests were performed at 37° C. using 20 units Pst I for 1 hr. followed by 5 units of Sau 3AI for 5 min. in a 20 μl reaction. The cleavage fragments were separated in 1.5% Agarose gel. An 854 base pair fragment was isolated which began with the nucleotide triplet encoding Asp at position 2 of rIFN-αA and terminated at the Pst I site 360 base pairs beyond the translation termination codon.

Using the procedure of Miyoshi, et al., Nucleic Acids Res. 8, 5507–5517 (1980), the synthetic oligodeoxynucleotides

were prepared and the 5' ends phosphorylated for ligation. The phosphorylated oligodeoxynucleotides were ligated to the Sau 3AI site of the truncated rIFN-αA DNA fragment (100 ng) in a volume of 7 μl at 15° C. for 16 hrs. in the presence of T4 ligase. After ligation, the ligase was inactivated by incubation at 70° C. for 10 min. and the DNA was digested with 50 units of Eco RI and 10 units of Pst I for 2 hrs. at 37° C. in 20 μl in order to regenerate the "sticky ends". The resultant 865 base pair dsDNA fragment, which contained the coding sequence for rIFN-αA (Gly 1), had an Eco RI site at the 5' end and a Pst I site at the 3' end of the coding region. The fragment was purified through a 1.5% Agarose gel and about 50 ng were recovered for cloning.

(b) Preparation of a Replicable Plasmidic Expression Vehicle for Producing rIFN-αA (Gly 1)

Figure 4:
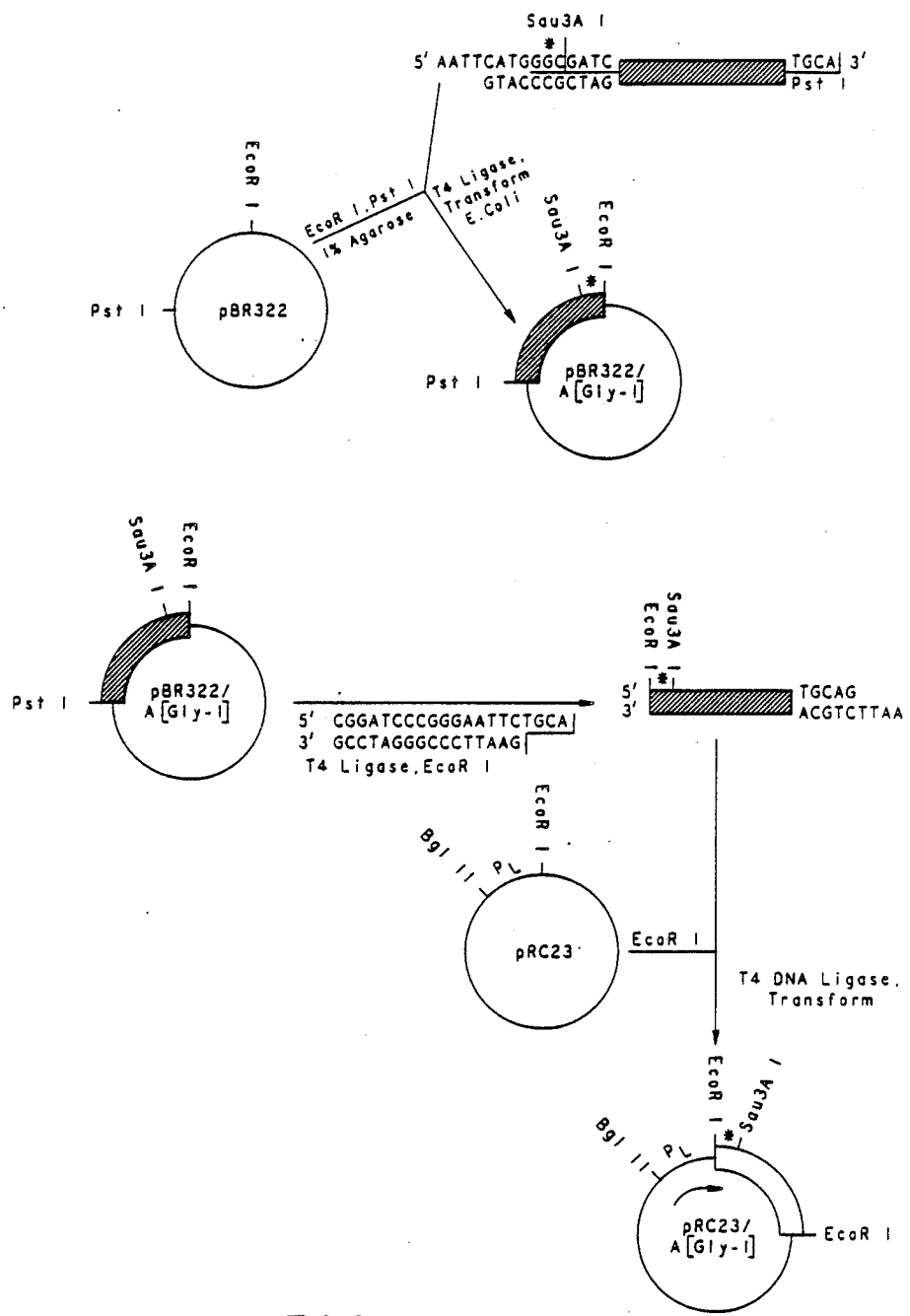
FIG. 4 is a schematic representation of the process used to produce the replicable plasmidic expression vehicle for expression of rIFN-αA (Gly 1).

FIG. 4 is a schematic representation of the procedure which was employed to prepare the expression vehicle. We employed plasmid pRC 23 as the expression vector to prepare the replicable plasmidic expression vehicle for producing rIFN-αA (Gly 1). As previously indicated, this plasmid was derived from pBR 322 and contained a $P_L$ promoter-operator. Since pRC 23 was designed to accept genes on an Eco RI restriction site, it was necessary to convert the 3' Pst I site of the 865 base pair fragment to an Eco RI site. In order to have a sufficient amount of the fragment to perform the modification, we first cloned the 865 base pair fragment, using plasmid pBR 322, which contains a tetracycline resistance gene, as a cloning vector. We digested 500 ng of pBR 322 to completion at 37° C. with 10 units each of Eco RI and Pst I in a 20 μl reaction. The linearized vector thus produced was purified through a 1.0% Agarose gel. The 865 base pair fragment encoding rIFN-αA (Gly 1) (50 ng) was ligated with 100 ng of the linearized pBR 322 using T4 ligase in 10 μl for 8 hrs. at 15° C. After ligation, the mixture was incubated at 70° C. for 10 min. and used to transform a competent MC 1061 strain of *E. coli* cells. The cells were plated out on LB agar containing 10 μg/ml of tetracycline and the tetracycline resistant colonies obtained from incubation at 37° C. were screened for the presence of the plasmid pBR 322/rIFN-αA (Gly 1). Plasmid screening was performed by the alkaline lysis procedure of Birnboim, H. C. and Doly, J., Nucleic Acids Res. 7, 1513 (1979).

Synthetic oligodeoxynucleotides having the sequences

were prepared by the procedure described in Miyoshi, et al., Nucleic Acids Res. 8, 5507–5517 (1980) and phosphorylated with ATP in the presence of polynucleotide kinase at the 5' ends for ligation.

The plasmid pBR 322/rIFN-αA (Gly 1) (200 ng), which contained the 865 base pair insert encoding rIFN-αA (Gly 1), was digested to completion with 20 units of Pst I at 37° C. for 1 hr. and the linearized vector was purified through a 1.0% Agarose gel and recovered from the gel. The synthetic oligodeoxynucleotides (50 ng each) were ligated to 200 ng of the linearized vector in a volume of 5 μl at 15° C. for 16 hrs. After ligase inactivation, the resultant dsDNA was digested with 50 units of Eco RI for 3 hrs. at 37° C. An 869 base pair fragment encoding rIFN-αA (Gly 1) and terminating in an Eco RI site at either end, was purified on 1.0% Agarose gel and recovered for cloning into the Eco RI site of pRC 23.

About 500 ng of pRC 23 was digested to completion with 10 units of Eco RI at 37° C. for 1 hr. in 20 μl. There was added 1 μg of calf intestinal alkaline phosphatase to dephosporylate the Eco RI ends of the plasmid and incubation was continued for an additional 30 min. The reaction was terminated by heating at 68° C. for 10 min. and the linearized vector was purified through a 1.0% Agarose gel and recovered. The linearized vector (100 ng) was ligated with 50 ng of the 869 base pair fragment encoding rIFN-αA (Gly 1) in 10 μl at 15° C. for 10 hrs. to produce the replicable plasmidic expression vehicle pRC 23/rIFN-αA (Gly 1).

(c) Preparation of Transformant Containing pRC 23/rIFN-αA (Gly 1)

The ligation mixture was used to transform an RR1 strain of E. coli cells which contained the compatible plasmid pRK 248 cIts as described by Bernard, H. U. and Helinski, D. R, Methods in Enzymology, 18, 482. The compatible plasmid encodes the production of the repressor protein which recognizes and binds the operator portion of the $P_L$ promoter-operator on pRC 23. The E. coli cells were transformed at 4° C. for 30 min. in the presence of 50 mmol $CaCl_2$ The cells were plated out at 30° C. on LB agar containing ampicillin (50 μg/ml). The pRC 23 plasmid contains a gene for ampicillin resistance. After incubation the ampicillin resistant colonies were selected and screened for the presence of the plasmid pRC 23/rIFN-αA (Gly 1) with the gene inserted in the proper orientation relative to the $P_L$ promoter.

(d) Expression and Purification of rIFN-αA (Gly 1)

A colony of transformants containing the plasmid pRC 23/rIFN-αA (Gly 1) and the compatible plasmid was grown up in 2 ml of LB agar containing ampicillin (50 μg/ml) at a temperature which was not allowed to exceed 30° C. When the $OD_{600}$ of the culture reached 0.6, the temperature was raised to 42° C. to inactivate the repressor protein and initiate expression. After 2 hrs. at 42° C. the cells were harvested and lysed in 50 μl of 7M Guanidine-HCl at 0° C. for 10 min. Extracts were centrifuged for 5 min. at 12,000 g. The supernatants were diluted 1:100 for antiviral assay.

The rIFN-αA (Gly 1) was extracted from E. coli cell paste using an extraction buffer containing 2M Guanidine-HCl, 2% Triton×100, 0.1M Tris-Cl, pH 7.5, for 2 hrs. at 4° C. The extraction mixture was diluted fivefold with cold distilled water, centrifuged at 10,000×g. for 1 hr. and purified on a 1×2-cm immunoaffinity chromatography column. The immunoaffinity column was packed with 1.0 ml of Agarose gel to which there was covalently bound approximately 13 mg of a monoclonal antibody to rIFN-αA. Preparation of the monoclonal antibody, identified as Li-8, is described by Staehelin et al. in J. Biol. Chem., 256, 9750 (1981).

The rIFN-αA/Gly 1-containing extraction buffer (20 ml) was loaded onto the column, which was operated at a flow rate of 1.0 ml/min. or less. The column was then sequentially washed with 5 bed-volumes of the solutions containing 1. 0.286M Guanidine-HCl; 0.286% Triton x-100; 0.1M Tris-Cl, pH 7.5
2. 0.5M NaCl; 0.2% Triton x-100; 0.025M Tris-Cl, pH 7.5
3. 1.0M sodium thiocyanate; 0.1% Triton x-100; 0.025M Tris-Cl, pH 7.5
4. 0.15M NaCl; 0.1% Triton x-100.

The rIFN-αA (Gly 1) was then eluted from the column using an elution solvent of 0.2M acetic acid, 0.15M NaCl and 0.1% Triton x-100 at pH 2.5.

The eluate from the immunoaffinity chromatography column was tested for antiviral activity against vesicular stomatitis virus using the cytopathic effect inhibition test described in Familletti, et al., supra. The specific activity of the eluate containing the rIFN-αA (Gly 1) was $2 \times 10^8$ units/mg of protein, which corresponds to that of rIFN-αA.

Prior to raising the temperature to 42° C. to initiate expression, an aliquot of the culture containing the transformants was set aside and stored in glycerol at 30° C. This aliquot was then grown up in a 10-liter fermentor containing LB agar containing ampicillin 50 μg/ml at a temperature not exceeding 30° C. until the $OD_{600}$ reached between 4 and 5. The temperature was then raised to 42° C. to initiate expression. After the $OD_{600}$ reached about 12 (2–3 hrs), the rIFN-αA (Gly 1) was recovered and purified in a manner similar to that described above for the 2-ml culture. The purified rIFN-αA (Gly 1) obtained from the 10-liter culture had an antiviral activity on MDBK cells of $3.3 \times 10^8$ ($\pm 0.76 \times 10^8$) units/mg of protein.

Figure 5:
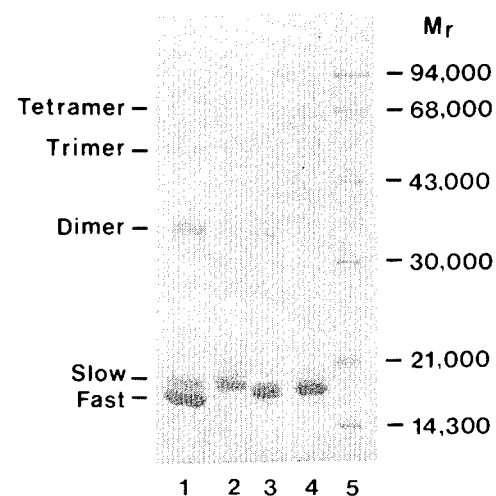
FIG. 5 is a photographic representation of a sodium dodecylsulfate polyacrylamide gel on which rIFN-αA and rIFN-αA (Gly 1) were electrophoresced for detection of oligomers.

The purified rIFN-αA (Gly 1) eluate from the immunoaffinity chromatography column was electrophoresced on sodium dodecylsulfate polyacrylamide gel under non-reducing conditions. FIG. 5 is a photograph of the gel. Track 1, which is a sample of rIFN-αA, displayed two bands corresponding to a slow-moving monomer and a fast-moving monomer, as well as dimer, trimer and tetramer. Track 2, which is a sample of rIFN-αA (Gly 1), displayed only slow-moving monomer and a small amount of dimer. Track 3, which represents rIFN-αA (Gly 1) which has been neutralized to pH 7.0 shows an increase in the dimer from due to pH-dependent dusulfide bond formation between cysteines at position 98. Track 4 represents a sample of the material from track 3 reduced with β-mercaptoethanol and demonstrates that the dimer is a result of disulfide bond formation.

EXAMPLE 2

Preparation of rIFN-αA (Gly 1/Ser 98)

(a) Preparation of dsDNA Encoding rIFN-αA (Gly 1/Ser 98)

We prepared the dsDNA encoding rIFN-αA (Gly 1/Ser 98) by taking advantage of a Pvu II site upstream of the nucleotide triplet in the rIFN-αA (Gly 1) gene encoding the cysteine at position 98 and a Hinf I site downstream of the nucleotide triplet. The Pvu II site and the Hinf I site are separated by 48 bases on the coding strand.

Referring to FIG. 3, we employed as a starting material pRC 23/rIFN-αA (Gly 1) which contained the 869 base pair insert of Example 1 encoding rIFN-αA (Gly 1). We cleaved this 869 base pair segment out of pRC 23 by digesting to completion with 20 units of Eco-RI and 20 units of Pvu II for 2 hrs. at 37° C. in 20 μl. The 869 base pair segment was thus cleaved out of pRC 23/rIFN-αA (Gly 1) at the Eco RI sites and was itself cleaved at the Pvu II site just upstream of the nucleotide triplet encoding cysteine at position 98 in two fragments—a 273 base pair fragment containing the 5' end of the rIFN-αA (Gly 1) gene and a 596 base pair segment containing the 3' end of the gene including the nucleotide triplet encoding cysteine at position 98. The 596 base pair fragment was partially digested with 5 units of Hinf I at 37° C. for 5 min. in 20 μl. Hinf I was inactivated immediately at 70° C. for 10 min. A 548 base pair Hinf I-Eco RI fragment containing the 3' end of the rIFN-αA (Gly 1) gene was isolated and purified on 1.5% Agarose gel eliminating a 48 base pair fragment containing the triplet encoding the cysteine at position 98.

Using the procedure of Miyoshi, supra, two double stranded synthetic oligodeoxynucleotides having a complementary overlapping sequence at the 3' end of the coding strand of the first oligodeoxynucleotide and the 5' end of the coding strand of the second oligodeoxynucleotide were prepared. When ligated at the complementary sequence, these two oligodeoxynucleotides produced a 48 base pair insert which was identical to the 48 base pair fragment cleaved out of the rIFN A (Gly 1) gene except that the nucleotide triplet encoding cysteine at position 98 was replaced by an AGC nucleotide triplet encoding serine.

The two double stranded synthetic oligodeoxynucleotides had the following nucleotide sequences:

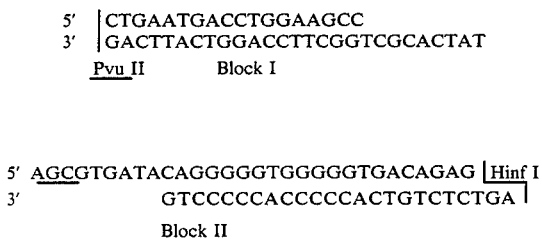

Prior to annealing the individual strands together to produce the two double strands, the 5' ends were phosphorylated with ATP using polynucleotide kinase to allow ligation. Block I (50 ng) was ligated to the Pvu II site of the 273 base pair cleavage fragment at the 5' end of the rIFN-αA (Gly 1) gene (300 ng) for 16 hrs. at 15° C. in a 7 μl reaction. Block II (50 ng) was then ligated to the Hinf I site of the 548 base pair cleavage fragment at the 3' end of the rIFN-αA (Gly 1) gene (100 ng) for 16 hrs. at 15° C. in a 7 μl reaction. The two dsDNA fragments produced by these ligations were then ligated to each other at the 9 base pair complementary overlapping portions of Block I and Block II for 16 hrs. at 15° C. The resultant 869 base pair dsDNA encoding rIFN-αA (Gly 1/Ser 98) was isolated and purified on a 1.5% Agarose gel. The dsDNA had an Eco RI recognition site at either end.

(b) Preparation of a Replicable Plasmidic Expression Vehicle for Producing rIFN-αA (Gly 1/Ser 98)

Figure 6:
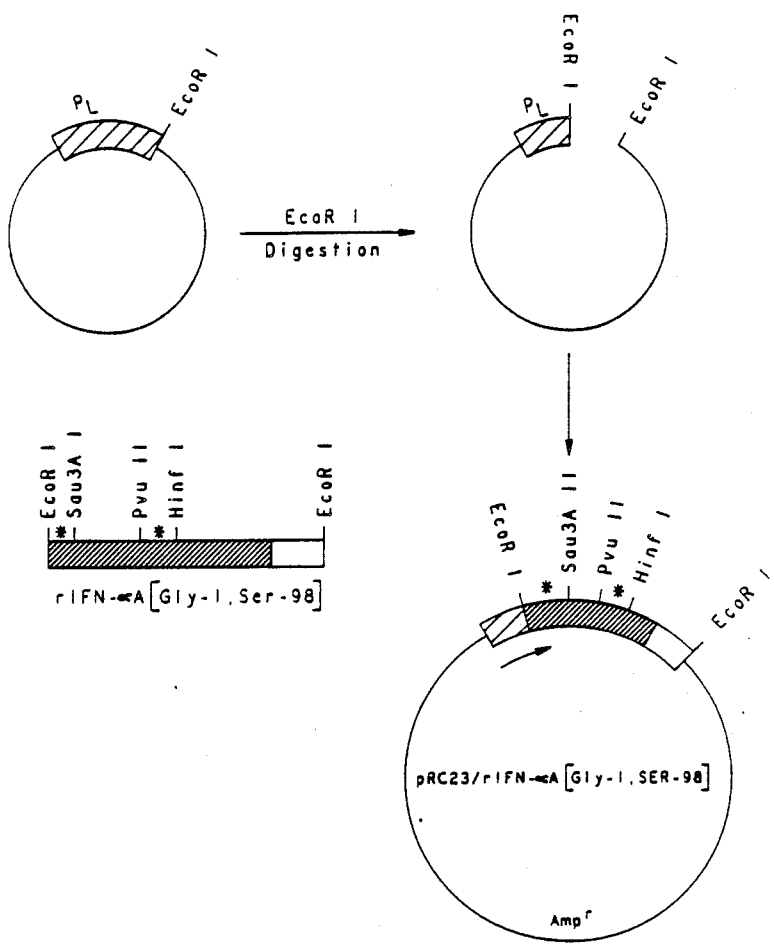
FIG. 6 is a schematic representation of the process used to prepare the replicable plasmidic expression vehicle for expression of rIFN-αA (Gly 1/Ser 98).

FIG. 6 is a schematic representation of the procedure which was employed to prepare the expression vehicle. Plasmid pRC 23 (500 ng) was digested to completion with 10 units of Eco RI at 37° C. for 1 hr. in 20 μl. There was then added 1 μg of calf intestinal alkaline phosphatase and incubation was continued an additional 30 min. The reaction was terminated by heating at 68° C. for 10 min. and the linearized vector was purified through a 1.5% Agarose gel and recovered. The linearized vector (100 ng) was ligated with 50 ng of the 869 base pair fragment encoding rIFN-αA (Gly 1/Ser 98) in 7 μl for 10 hrs. at 15° C. to produce the replicable plasmidic expression vehicle pRC 23/rIFN-αA (Gly 1/Ser 98).

(c) Preparation of Transformant Containing pRC 23/rIFN-αA (Gly 1/Ser 98)

The ligation mixture was used to transform an RR1 strain of E. coli containing the compatible plasmid pRK 248 cIts, encoding the production of the temperature-sensitive repressor protein which recognizes and binds the operator sequence of $P_L$ promoter-operator on pRC 23. The E. coli cells were transformed at 4° C. for 20 min. in the presence of 50 mmol $CaCl_2$. Ampicillin resistant colonies resulting from overnight incubation at 30° C. on LB plates were selected and inoculated into 2-ml cultures of LB agar containing ampicillin (50 μg/ml). Colonies containing the recombinant plasmid pRC 23/rIFN-αA (Gly 1/Ser 98) with the gene inserted in the proper orientation relative to the $P_L$ promoter were selected by screening with the alkaline lysis method (Birnboim, supra).

(d) Expression and Purification of rIFN-αA (Gly 1/Ser 98)

A colony of transformants containing the plasmid pRC 23/rIFN-αA (Gly 1/Ser 98) and the compatible plasmid was grown up in 10 liters of LB agar and ampicillin (50 μg/ml) at a temperature which was not allowed to exceed 30° C. When the $OD_{600}$ of the culture reached 0.6, the temperature was raised to 42° C. to inactivate the repressor protein and initiate expression. After 2 hrs. at 42° C. the cells were harvested and lysed.

The rIFN-αA (Gly 1/Ser 98) was extracted from E. coli cell paste using 4 volumes of the buffer of Example 1(d) and purified on a 1.6×5.0-cm immunoaffinity chromatography column. The immunoaffinity chromatography column was packed with 10 ml of Agarose gel to which there was covalently bound approximately 130 mg of a monoclonal antibody to rIFN-αA. Preparation of the monoclonal antibody, identified as Li-8, is described by Staehelin et al. in J. Biol. Chem., 256, 9750 (1981).

The rIFN-αA/(Gly 1/Ser 98)-containing extraction buffer (5,000 ml) was loaded onto the column, which was operated at a flow rate of 5.0 ml/min. or less. The column was then sequentially washed with 5 bed-volumes of the same washing solutions employed in Example 1(d). The rIFN-αA (Gly 1/Ser 98) was then eluted from the column using the same elution solvent as in Example 1(d).

The eluate from the immunoaffinity chromatography column was tested for antiviral activity against vesicular stomatitis virus using the cytopathic effect inhibition test described in Familletti, supra. The specific activity of the eluate containing the rIFN-αA (Gly 1/Ser 98) was $2 \times 10^8$ units/mg of protein, which corresponds to that of rIFN-αA.

Figure 7:
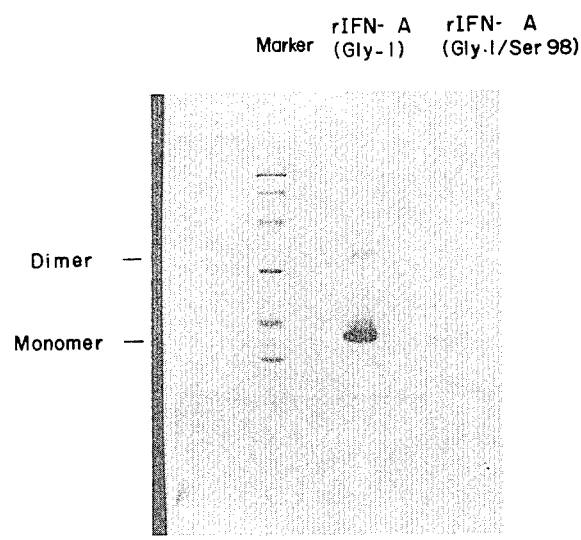
FIG. 7 is a photographic representation of a sodium dodecylsulfate polyacrylamide gel on which rIFN-αA (Gly 1) and rIFN-αA (Gly 1/Ser 98) were electrophoresced for detection of oligomers.

The purified rIFN-αA (Gly 1/Ser 98) eluate from the immunoaffinity chromatography column was electrophoresced on sodium dodecylsulfate polyacrylamide gel under non reducing conditions. FIG. 7 is a photograph of the gel. The sample of rIFN-αA (Gly 1/Ser 98), displayed a single band of monomeric interferon, whereas Track 2, which is a sample of rIFN-αA, displayed bands corresponding to monomer, dimer, trimer and higher oligomers.

We claim:

1. An antiviral composition comprising a biologically active recombinant or hybrid recombinant human IFN-α in which at least one cysteine residue at position 1, 98, 99 or 100 has been replaced by an amino acid residue that is incapable of forming a disulfide bond, and a pharmaceutically acceptable carrier vehicle.

2. The antiviral composition of claim 1 in which the IFN-α is a recombinant human IFN-αA in which at least one cysteine residue at position 1 or 98 has been replaced.

3. A double-stranded DNA comprising a coding strand and a complementary strand, which coding strand comprises a series of nucleotide triplets encoding a biologically active recombinant or hybrid recombinant human IFN-α in which at least one cysteine residue at position 1, 98, 99 or 100 has been replaced by an amino acid residue that is incapable of forming a disulfide bond.

4. The double-stranded DNA of claim 3 in which the coding strand, reading from the 5' end, comprises the sequence X—GAT—CTG—CCT—CAA—ACC—CAC—AGC—CTG—
GGT—AGC—AGG—AGG—ACC—TTG—ATG—CTC—
CTG—GCA—CAG—ATG—AGG—AAA—ATC—TCT—
CTT—TTC—TCC—TGC—TTG—AAG—GAC—AGA—
CAT—GAC—TTT—GGA—TTT—CCC—CAG—GAG—
GAG—TTT—GGC—AAC—CAG—TTC—CAA—AAG—
GCT—GAA—ACC—ATC—CCT—GTC—CTC—CAT—
GAG—ATG—ATC—CAG—CAG—ATC—TTC—AAT—
CTC—TTC—AGC—ACA—AAG—GAC—TCA—TCT—
GCT—GCT—TGG—GAT—GAG—ACC—CTC—CTA—
GAC—AAA—TTC—TAC—ACT—GAA—CTC—TAC—
CAG—CAG—CTG—AAT—GAC—CTG—GAA—GCC—
Y—GTG—ATA—CAG—GGG—GTG—GGG—GTG—
ACA—GAG—ACT—CCC—CTG—ATG—AAG—GAG—
GAC—TCC—ATT—CTG—GCT—GTG—AGG—AAA—
TAC—TTC—CAA—AGA—ATC—ACT—CTC—TAT—
CTG—AAA—GAG—AAG—AAA—TAC—AGC—CCT—
TGT—GCC—TGC—GAG—GTT—GTC—AGA—GCA—
GAA—ATC—ATG—AGA—TCT—TTT—TCT—TTG—
TCA—ACA—AAC—TTG—CAA—GAA—AGT—
TTA—AGA—AGT—AAG—GAA, wherein X and Y encode cysteine or an amino acid residue that is incapable of forming a disulfide bond.

5. The double-stranded DNA of claim 4 in which X encodes a glycine residue.

6. The double-stranded DNA of claim 4 in which Y encodes a serine residue.

7. The double-stranded DNA of claim 4 in which X is the nucleotide triplet -GGC-.

8. The double-stranded DNA of claim 4 in which Y is the nucleotide triplet -AGC-.

9. A replicable plasmidic expression vehicle comprising:
  (a) a replicon;
  (b) a promoter-operator sequence;
  (c) a DNA sequence encoding a ribosome binding site;
  (d) a DNA sequence, in phase with said promoter-operator sequence, comprising a translation initiation signal, a sequence encoding a biologically active recombinant or hybrid recombinant human IFN-α in which at least one cysteine residue at position 1, 98, 99 or 100 has been replaced by an amino acid residue that is incapable of forming a disulfide bond, and a translation termination signal.

10. The replicable plasmidic expression vehicle of claim 9 in which the IFN-α encoded is a recombinant human IFN-αA in which at least one cysteine residue at position 1 or 98 has been replaced.

11. The replicable plasmidic expression vehicle of claim 9 in which the IFN-α encoded is a recombinant IFN-αD or a hybrid recombinant IFN-α having an IFN-αD amino acid subsequence, which interferons normally contain a cysteine residue at position 87, in which such residue has been replaced by a serine residue.

12. The replicable plasmidic expression vehicle of claim 9 in which the sequence encoding the IFN-α, reading from the 5' end, comprises the sequence X—GAT—CTG—CCT—CAA—ACC—CAC—AGC—CTG—
GGT—AGC—AGG—AGG—ACC—TTG—ATG—CTC—
CTG—GCA—CAG—ATG—AGG—AAA—ATC—TCT—
CTT—TTC—TCC—TGC—TTG—AAG—GAC—AGA—
CAT—GAC—TTT—GGA—TTT—CCC—CAG—GAG—
GAG—TTT—GGC—AAC—CAG—TTC—CAA—AAG—
GCT—GAA—ACC—ATC—CCT—GTC—CTC—CAT—
GAG—ATG—ATC—CAG—CAG—ATC—TTC—AAT—
CTC—TTC—AGC—ACA—AAG—GAC—TCA—TCT—
GCT—GCT—TGC—GAT—GAG—ACC—CTC—CTA—
GAC—AAA—TTC—TAC—ACT—GAA—CTC—TAC—
CAG—CAG—CTG—AAT—GAC—CTG—GAA—GCC—
Y—GTG—ATA—CAG—GGG—GTG—GGG—GTG—
ACA—GAG—ACT—CCC—CTG—ATG—AAG—GAG—
GAC—TCC—ATT—CTG—GCT—GTG—AGG—AAA—
TAC—TTC—CAA—AGA—ATC—ACT—CTC—TAT—
CTG—AAA—GAG—AAG—AAA—TAC—AGC—CCT—
TGT—GCC—TGC—GAG—GTT—GTC—AGA—GCA—
GAA—ATC—ATG—AGA—TCT—TTT—TCT—TTG—
TCA—ACA—AAC—TTG—CAA—GAA—AGT—
TTA—AGA—AGT—AAG—GAA, wherein X and Y encode cysteine or an amino acid residue that is incapable of forming a disulfide bond.

13. The replicable plasmidic expression vehicle of claim 12 in which X encodes a glycine residue.

14. The replicable plasmidic expression vehicle of claim 13 in which Y encodes a serine residue.

15. The replicable plasmidic expression vehicle of claim 12 in which X is the nucleotide triplet -GGC-.

16. The replicable plasmidic expression vehicle of claim 12 in which Y is the nucleotide triplet -AGC-.

17. A microorganism containing the replicable plasmidic expression vehicle of claim 9.

* * * * *